United States Patent
Romano et al.

(10) Patent No.: US 11,376,160 B2
(45) Date of Patent: Jul. 5, 2022

(54) COUPLING INTERFACE BETWEEN A LASER SOURCE AND A TISSUE TO BE TREATED

(71) Applicant: KERANOVA, Saint Etienne (FR)

(72) Inventors: Fabrizio Romano, Beynost (FR); Aurelien Bernard, Saint Etienne (FR)

(73) Assignee: KERANOVA, Saint Etienne (FR)

( * ) Notice: Subject to any disclaimer, the term of this patent is extended or adjusted under 35 U.S.C. 154(b) by 276 days.

(21) Appl. No.: 16/485,975

(22) PCT Filed: Feb. 23, 2018

(86) PCT No.: PCT/EP2018/054473
§ 371 (c)(1),
(2) Date: Aug. 14, 2019

(87) PCT Pub. No.: WO2018/154038
PCT Pub. Date: Aug. 30, 2018

(65) Prior Publication Data
US 2020/0229972 A1 Jul. 23, 2020

(30) Foreign Application Priority Data

Feb. 24, 2017 (FR) ...................................... 1751469

(51) Int. Cl.
*A61F 9/009* (2006.01)
*A61F 9/007* (2006.01)
*A61F 9/008* (2006.01)

(52) U.S. Cl.
CPC .............. *A61F 9/009* (2013.01); *A61F 9/008* (2013.01); *A61F 9/00745* (2013.01);
(Continued)

(58) Field of Classification Search
CPC ...... A61F 9/009; A61F 9/00745; A61F 9/008; A61F 2009/0087; A61F 2009/00872; A61B 2217/005; A61B 2217/007
(Continued)

(56) References Cited

U.S. PATENT DOCUMENTS 5,548,352 A * 8/1996 Dewey .................... A61B 3/125
351/159.02
2010/0274228 A1 * 10/2010 Mrochen ................. A61F 9/008
604/541

(Continued)

FOREIGN PATENT DOCUMENTS

CN 102625685 A 8/2012
EP 1970034 A1 9/2008
(Continued)

*Primary Examiner* — Aaron F Roane
(74) *Attorney, Agent, or Firm* — BCF LLP (57) ABSTRACT

The present invention relates to a coupling interface between a laser source and a tissue (2) to be treated, characterized in that the coupling interface comprises —a ring (3) including: •a side wall (31), •a proximal end (311) intended to come into contact with the tissue (2) to be treated, and •a distal end (312) intended to receive the end of the laser source; —a window (32) transparent to a laser beam generated by the laser source, said window being mounted in a sealed manner on the distal end (312) of the ring (3) in such a way as to close the distal end (312) of the ring (3).

19 Claims, 4 Drawing Sheets

(52) U.S. Cl.
CPC ... *A61B 2217/005* (2013.01); *A61B 2217/007* (2013.01); *A61F 2009/0087* (2013.01); *A61F 2009/00872* (2013.01)

(58) Field of Classification Search
USPC .......................................................... 606/4
See application file for complete search history.

(56) References Cited

U.S. PATENT DOCUMENTS

| | | | |
|---|---|---|---|
| 2011/0178512 A1* | 7/2011 | Blumenkranz | A61F 9/0084 606/6 |
| 2011/0319873 A1 | 12/2011 | Raksi et al. | |
| 2012/0277663 A1 | 11/2012 | Millman et al. | |
| 2016/0287332 A1 | 10/2016 | Griffits | |

FOREIGN PATENT DOCUMENTS

| | | |
|---|---|---|
| KR | 10-2013-0078575 A | 7/2013 |
| WO | 2017055252 A1 | 4/2017 |

* cited by examiner

COUPLING INTERFACE BETWEEN A LASER SOURCE AND A TISSUE TO BE TREATED

CROSS-REFERENCE TO RELATED APPLICATIONS

This application is a national phase filing under 35 U.S.C. § 371 of International Application No. PCT/EP2018/054473 filed on Feb. 23, 2018, which claims benefit of priority from French Patent Application No. 1751469 filed on Feb. 24, 2017, the contents of each of which are hereby incorporated by reference in their entirety.

TECHNICAL FIELD

The present invention relates to the technical field of surgical operations performed by laser, and more particularly to the field of ophthalmic surgery in particular for applications of cutting corneas or crystalline lenses.

The invention relates to an adaptation interface for coupling a laser source to human or animal tissue to be treated, such as a cornea or a crystalline lens.

By "laser source" is meant a light source capable of emitting a L.A.S.E.R. beam in the form of ultra-short pulses, whose duration is comprised between 1 femtosecond and 100 picoseconds, preferably comprised between 1 and 1000 femtoseconds, in particular in the order of one hundred femtoseconds.

PRIOR ART

It is known from the state of the art to perform surgical operations of the eye by means of a laser source, such as operations of cutting corneas or crystalline lenses.

A laser source is an instrument capable of cutting the corneal tissue, for example, by focusing a L.A.S.E.R. beam in the stroma of the cornea, and by making a succession of small adjacent cavitation bubbles, which then form a cutting line.

More precisely, during the focusing of the L.A.S.E.R. beam in the cornea, a plasma is generated by non-linear ionization when the intensity of the laser source exceeds a threshold value, called optical breakdown threshold. A cavitation bubble is then formed, causing a very localized disruption of the surrounding tissues. Thus, the volume actually ablated by the laser source is very small compared to the disrupted area.

In order to allow the coupling of the laser source to a patient's eye, it is known to use an adaptation interface disposed between the patient's eye and the laser source.

Such a coupling interface makes it possible to hold the eyeball in a stable and constant position, centered and at a known distance from the laser source, while avoiding any movement, throughout the duration of a treatment.

Figure 1:
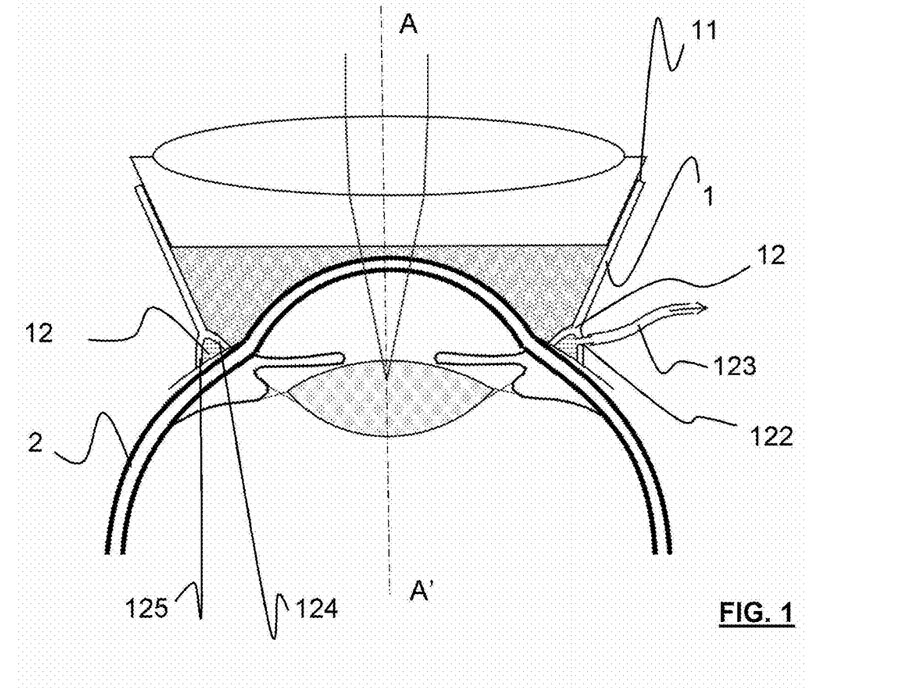
FIGS. 1, 2 and 4B are schematic representations of a coupling interface of the prior art.

1. Coupling Interface Known in the Prior Art 1.1. First Example of an Existing Coupling Interface FIG. 1 illustrates a first example of a coupling interface of the prior art. The coupling interface comprises a ring including a truncated cone 1 of axis A-A'. The truncated cone 1 is open at its both ends. The large base 11 of the truncated cone 1 is intended to receive the end of the laser source. The small base of the truncated cone 1 is intended to come into contact with the eye 2. The coupling interface also comprises:

- an annular gas flow groove 12 extending on the periphery of the small base, and
- a tubular access member 122 extending radially outwardly and allowing the connection of the annular groove 12 to an outer aspiration device (not represented) via a connection nozzle 123.

The annular groove 12 has a U-shaped section defined by two circular rims 124, 125 intended to be pressed against the patient's eye 2. The aspiration device is known per se to those skilled in the art and allows creating a vacuum in the annular groove 12 once the circular rims 124, 125 are applied to the eye 2. The generation of a vacuum in the annular groove 12 allows securing the coupling interface on the eye 2 by suction effect throughout the entire duration of the treatment.

1.2. Principle of Operation of the First Example of an Existing Coupling Interface The principle of operation of such a coupling interface is as follows.

At first, the practitioner places the ring of the coupling interface on the eye 2.

Once the ring is correctly positioned and centered, the aspiration device is activated to generate a vacuum in the space defined between the annular groove 12 and the eye 2 in order to secure the coupling interface on the eye 2 by suction.

When the ring is secured to the eye 2, the ring is filled with a liquid having a refractive index close to that of the cornea until immersion of the cornea. The liquid thus immersing the cornea, has the advantage of simplifying the trajectory of the L.A.S.E.R. beams through the cornea, these passing through a planar surface, rather than a curved surface, the patient's cornea, which moreover is often affected by minor optical defects (astigmatism) adding possible aberrations on the L.A.S.E.R beam path.

The laser source is then placed to the right of the coupling interface, the distal portion of the laser source being inserted and locked on the coupling interface, so that the eye 2 and the optical axis of the laser are aligned and securely held throughout the duration of the treatment.

1.3. Disadvantages of the First Example of an Existing Coupling Interface

Such a coupling interface has many disadvantages.

1.3.1. Pressure Exerted on the Interface to Ensure the Sealing

Particularly, the efficiency of the suction of the coupling interface on the eye 2 depends on the quality of the sealing between the circular rims 124, 125 and the eye 2.

A perfect contact must therefore be obtained over the entire circumference of the line of contact of each circular rim 124, 125.

This is not always simple, the patients' eyes being all different, the surface of the eyeball does not necessarily follow the slope between each circular rim 124, 125.

In order to overcome this inhomogeneity between the eyes of the patients, it is therefore necessary to strongly press the ring of the coupling interface to obtain a good sealing between the groove 12 and the eye 2, which is detrimental to the patient's comfort and safety. Indeed, the force exerted on the ring of the coupling interface to obtain a satisfactory sealing tends to enter the circular rims 124, 125 in the conjunctiva.

The force to be applied for achieving the sealing is sometimes so significant that the discomfort of the patient can tend to be painful. Moreover, this pressure, even though it is of short duration, immediately causes the increase of the intraocular pressure of the patient which, in some patients at risk (high myopia, retinal detachment history or glaucoma), may result in serious side effects.

1.3.2. Time Needed to Obtain a Vacuum

Moreover, as previously described, the suction of the coupling interface on the eye 2 is obtained by using an aspiration device generating a vacuum in the space delimited between the groove 12 and the eye 2.

Since a gas is compressible and extensible, the aspiration force depends on the volume of gas comprised in this sealed space. The larger this volume, the more the aspiration force increases slowly.

Some traditional coupling interfaces comprise nozzles fully filled with gas, which increases the time needed to obtain a satisfactory suction.

1.3.3. Level of the Vacuum

Also, the level of the vacuum must be significant in order to hold the coupling interface in position.

Indeed, in order to resist the ocular micro-movements and the tendency to un-suction, the aspiration force must be significant.

However, it is known that the aspiration force F is a function of the Vacuum P and the Surface S on which this vacuum is applied, namely:

$$F = P \times S.$$

In traditional coupling interfaces, the surface on which the vacuum is applied is small (i.e. limited to the surface of the eye between the two circular rims), it is necessary to apply a vacuum of significant value to obtain an aspiration force F allowing to resist the ocular micro-movements and the tendency to un-suction.

The importance of the applied vacuum sometimes leads to the appearance of conjunctival hemorrhage (effusion of red blood cells linked to the aspiration under the conjunctiva). Although superficial ecchymoses are generally very limited, and have no consequence for the vision, it is preferable to limit their appearance.

1.3.4. Manipulations

When the suction is obtained, the sucking ring becomes secured to the eyeball and the inverted open-air cone delimits a volume V that can be filled with a liquid of a refractive index close to that of the cornea, such as water or physiological saline.

This immersion step is usually performed manually by pouring into the cone a sufficient quantity of liquid to come up to the top of the cone.

With some traditional coupling interfaces, it is necessary to perform manipulations:

grab a bottle,
unscrew the cap,
stand upright and in sight to fill the cone,
pour enough liquid into the cone.

These manipulations are sometimes long and inaccurate, lengthening the suction time which must be reduced to the minimum.

1.3.5. Cost

Some traditional coupling interfaces work with specific surgical equipment. These had to integrate a suction system with pump, nozzles and vacuum sensor. Each system being specific, it is necessary to buy all these accessories. The present invention avoids to make this unnecessary expense. Indeed, this patient interface works with accessories already present in the operating room and in particular the phacoemulsification apparatus. The latter is equipped with an aspiration pump with vacuum sensor and an infusion line, and already has adequate nozzles. Our experimental tests demonstrate that the new coupling interface, object of this invention, works perfectly with a phacoemulsification apparatus, which generates a substantial saving for the customer.

Moreover, if the phacoemulsification apparatus, equipped with its pump system and with sensors is integrated into the laser equipment, this greatly simplifies the configuration in the operating room, a single machine allowing to perform the entire surgical procedure with a single consumable and a single aspiration/irrigation system which becomes a multifunctional system, ensuring firstly to perform the suction of the patient interface and secondly to complete the procedure with the irrigation/aspiration of the lenticular fragments and lenticular cortical masses.

1.2. Second Example of an Existing Coupling Interface

Figure 2:
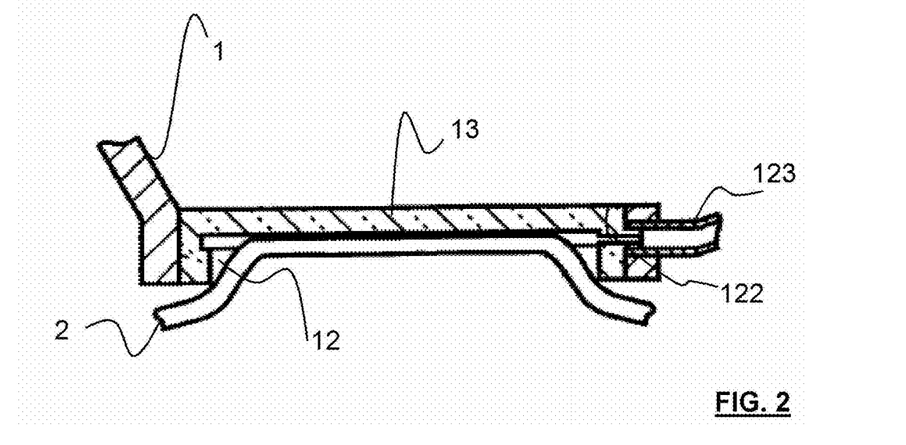

FIG. 2 illustrates a second example of a coupling interface of the prior art. This second example of a coupling interface differs from the first example in that the interface comprises a blade 13 transparent to laser radiation disposed in the vicinity of the small base of the truncated cone 1 intended to come into contact with the eye 2.

This blade 13 makes it possible to flatten the patient's cornea 2. Such applanation of the cornea is necessary when the coupling interface does not comprise liquid to reduce the corneal diopter. However, the applanation of the anterior face of the cornea (as represented in FIG. 2) induces the appearance of folds on the posterior surface of the cornea, these folds inducing a degradation of the quality of the laser treatment. Such a disadvantage related to the folding of the posterior face of the cornea is in particular described in the article entitled "*Optical patient interface in femtosecond laser-assisted cataract surgery: Contact corneal applanation versus liquid immersion*", by Jonathan H. Talamo, MD, Philip Gooding, MS, David Angeley, MS, William W. Culbertson, MD, Georg Schuele, PhD, Daniel Andersen, BS, George Marcellino, PhD, Emma Essock-Burns, PhD, Juan Batlle, MD, Rafael Feliz, MD, Neil J. Friedman, MD, Daniel Palanker, PhD.

2. Object of the Invention

An object of the present invention is to propose a coupling interface for overcoming at least one of the aforementioned drawbacks.

DISCLOSURE OF THE INVENTION

For this purpose, the invention proposes a coupling interface between a laser source and a tissue to be treated, remarkable in that the coupling interface comprises
a ring including:
 a side wall,
 a proximal end intended to come into contact with the tissue to be treated, and
 a distal end intended to receive the end of the laser source,
a window transparent to a laser beam generated by the laser source, said window being sealingly mounted on the ring so as to close the distal end of the ring,
an aspiration through channel extending between the inner and outer faces of the side wall, the aspiration channel being intended to be connected to an aspiration module for allowing the generation of a vacuum in an interior space defined between the window and the side wall,
an irrigation through channel extending between the inner and outer faces of the side wall, the irrigation channel being intended to be connected to an irrigation module for allowing the infusion of liquid into the interior space.

Thus, the present invention proposes to provide a coupling interface—in particular usable in the context of a laser ophthalmic surgery—with fast and painless suction and simultaneous and automatic infusion of liquid, this coupling interface being compatible with the use of irrigation and aspiration modules, which can be integrated into an apparatus commonly present in the ophthalmic operating room: the phacoemulsifier. Thus, the coupling interface can be used in a device including a laser source and a phacoemulsifier, this device comprising a single irrigation and aspiration module (pump+vacuum sensor) used for both the laser treatment and the phacoemulsification treatment. This makes it possible to limit the costs by integrating, in the same device, elements common to two specific modules (i.e. the laser source on the one hand and the phacoemulsifier on the other hand) usually separated in the operating room.

Of course, the present invention is also compatible with the use of non-integrated irrigation and aspiration modules, comprising for example one (or several) container(s) such as a syringe, one (or several) nozzle(s), and one (or several) pump(s) such as an electric syringe-pusher.

The presence of an irrigation channel opening into the space defined between the window and the side wall of the ring eliminates the need for applanation of the cornea to reduce the corneal diopter. It is thus possible to offset the window in the vicinity of the distal end of the ring in order to avoid any contact between the patient's eye and the window.

Preferred but non-limiting aspects of the coupling interface are as follows:
  the coupling interface may further comprise a bubble trap extending around the window;
  the bubble trap may consist of a circular inner groove extending between the side wall and the window;
  the aspiration channel can extend in a plane containing the window;
  the window may be covered with a layer of hydrophilic material;
  the window may have a non-planar geometry with parallel faces, having for example a concavity allowing better evacuation of the bubbles toward the bubble trap;
  the window may have a non-planar geometry with non-parallel faces, having for example a biconvexity, thus giving the window an optical role;
  The ring includes a flared neck of a generally frustoconical shape curved outwardly at its proximal end, the flared neck being capable of being applied to the outer surface of the tissue to be treated;
  the window can be attached to the ring by gluing;
  the internal diameter of the irrigation channel may be smaller than the internal diameter of the aspiration channel.

The invention also relates to a method for installing a coupling interface between a laser source and a tissue to be treated, the coupling interface comprising a ring including:
  a side wall,
  a proximal end intended to come into contact with the tissue to be treated,
  a distal end intended to receive the end of the laser source, and
  a window transparent to a laser beam generated by the laser source sealingly mounted on the distal end of the ring,
  the method comprising the following steps:
  Positioning the ring on the tissue to be treated
  Simultaneously activating a liquid aspiration device and a liquid irrigation device:
    activating the aspiration device allowing to create a vacuum in an interior space defined between the window, the side wall and the tissue to be treated,
    activating the irrigation device allowing to fill the interior space with liquid,
    Deactivating the irrigation device when the liquid is in contact with the window.
    Deactivating the aspiration pump as soon as the desired vacuum threshold is reached
    Holding the constant vacuum throughout the entire duration of the procedure.

Once the procedure is completed, the coupling interface is separated from the tissue to be treated by restoring the atmospheric pressure in the interior space defined between the window, the side wall and the treated tissue.

SHORT DESCRIPTION OF THE DRAWINGS

Other characteristics and advantages of the invention will clearly emerge from the description which is carried out hereinafter, for illustrative and non-limiting purposes, with reference to the appended figures, in which.

DETAILED DISCLOSURE OF THE INVENTION

The coupling interface according to the invention will now be described with reference to the figures. In these different figures, the equivalent elements are designated by the same reference numeral.

The coupling interface is intended to be disposed between a laser source and a target to be treated 2. The target 2 is for example a human or animal tissue to be treated such as an eyeball and more specifically a cornea or a crystalline lens.

In the remainder of the description, the invention will be described, by way of example, for the treatment of a cornea of a human or animal eye. Nevertheless, it is obvious to those skilled in the art that the coupling interface according to the invention can be used in other applications.

1. General Description of the Coupling Interface

Figure 3:
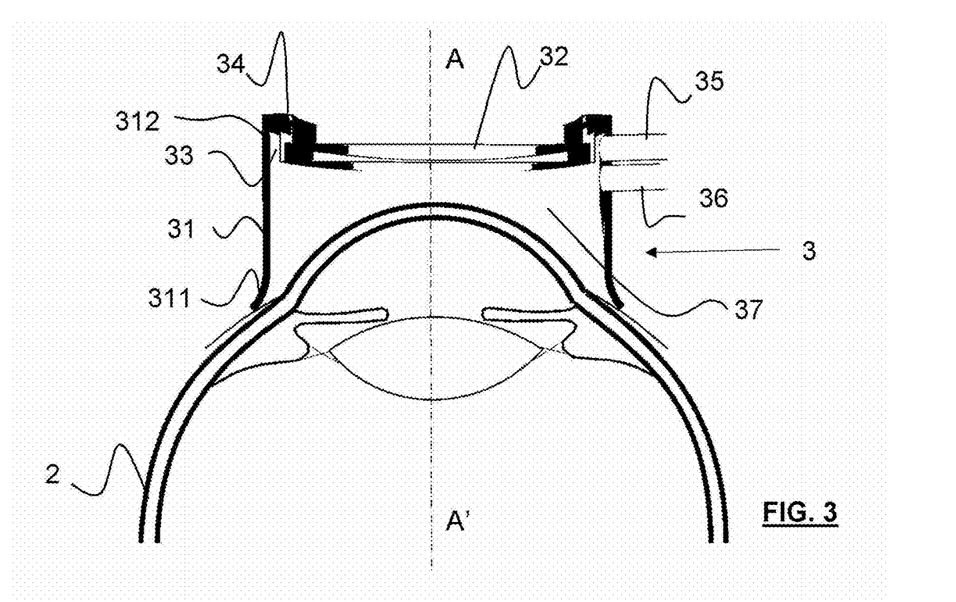
FIGS. 3, 4A, 5 and 6 are schematic representations of a coupling interface according to the invention.

With reference to FIG. 3, the coupling interface comprises a ring 3 including:
  a side wall 31 having a generally cylindrical or conical shape,
  a proximal end 311 intended to come into contact with an eye 2 to be treated, and
  a distal end 312 intended to receive the end of the laser source.

The coupling interface is remarkable in that it further comprises a window 32 transparent to the L.A.S.E.R. beam sealingly mounted on the distal end 312 of the ring 3 so as to close the distal end 312 of the ring 3. The ring 3 is therefore open only at its proximal end 311 intended to come into contact with the patient's eye 2.

The attachment of the coupling interface on the eye 2 of the patient can then be performed by generating a vacuum in the interior space 37 defined between:
  the side wall 31 of the ring 3,
  the transparent window 32, and
  the eye 2 of the patient.

Thus and unlike the existing coupling interfaces, the attachment of the coupling interface on the eye 2 by the generation of a vacuum, does not require a perfect bearing between two circular rims defining an annular groove.

Due to this new design, the level of vacuum necessary to hold the coupling interface in position is considerably reduced since the aspiration force applies this time to the entire surface of the eyeball covered by the ring 3.

Figure 4A:
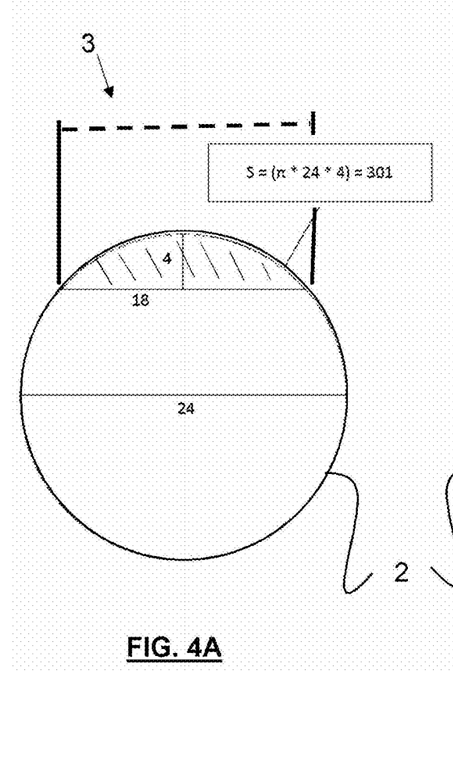
Figure 4B:
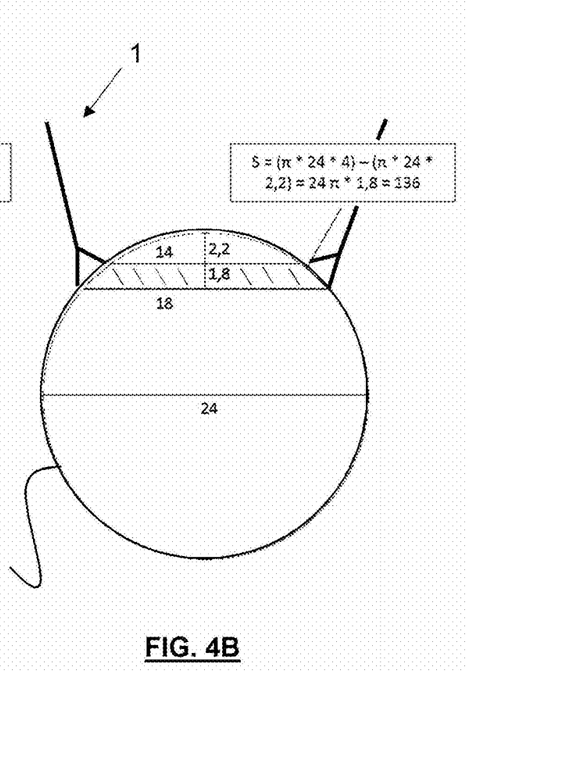

Indeed, as illustrated in FIG. 4B, which is a schematic representation of the traditional coupling interface of FIG. 1, in order to obtain an aspiration force, for example, of 3 Newtons, it is necessary to apply a vacuum of:

$$P=F/S,$$

namely $P=3/136.10^{-6}$, namely P=22058 Pa=0.22 bar=165 mmHg.

With the coupling interface illustrated in FIG. 3, for the same aspiration force of 3 Newtons, the required vacuum is only of:

$$P=F/S,$$

namely $P=3/301.10^{-6}$, namely P=9966 Pa=0.099 bar=74 mmHg (cf. FIG. 4A).

Thus, with the coupling interface illustrated in FIG. 3, the attachment of the ring 3 on the eye 2 is obtained by generating a vacuum much lower than the vacuum required for holding the traditional coupling interfaces.

2. Detailed Description of the Coupling Interface 2.1. Ring

In the embodiment illustrated in FIG. 3, the ring 3 includes a side wall 31 having a generally cylindrical shape. However, it is obvious to those skilled in the art that the ring 3 may have other shapes with symmetry of revolution about an axis A-A', such as a frustoconical shape.

The proximal end 311 of the ring 3 includes a flared neck of a generally frustoconical shape curved outwardly, and capable of being applied to the outer surface of the eye 2 in a non-traumatic manner. This flared neck has a concave profile of a radius of curvature substantially equal to the radius of curvature of the eye 2 allowing a tangential bearing.

The fact that the ring comprises a single flared neck (rather than two circular rims in the traditional coupling interfaces) makes it easy to achieve a perfect contact over the entire circumference of the contact line between the eye 2 and the ring 3.

The ring 3 comprises an annular crown 34 extending radially inwardly at its distal end 312. The annular crown 34 comprises a recess on its side face forming a cradle for receiving the transparent window 32. The recess makes it easy to place the transparent window 32. Any other method for sealingly attaching a transparent window on the distal portion, for example by welding, gluing or screwing, is of course conceivable.

The annular crown 34 also comprises a circular groove 33 extending between the side wall 31 and the transparent window 32. This circular groove 33 forms an air bubble trap. Indeed, air bubbles are likely to be formed during the filling of the coupling interface with the liquid having a refractive index close to that of the cornea. These air bubbles can affect the efficiency of the treatment, in particular if they are positioned on the propagation path of the L.A.S.E.R. beam emitted by the laser source. The presence of an air bubble trap makes it possible to retain the air bubbles generated during the filling of the coupling interface out of the propagation path of the L.A.S.E.R. beam. This ensures good treatment efficiency to the practitioner. This can also be facilitated by a non-planar geometry of the transparent window, for example with a convexity towards the eye 2, while keeping parallel faces, so as to improve the conveyance of gas bubbles toward this groove.

2.2. Window

With reference to FIG. 3, the window 32 transparent to the beam generated by the laser source has the shape of a disk. Of course, the window may have other shapes (square, rectangular, elliptical shapes) depending on the intended application.

The window 32 may be designed in different materials such as glass or plastic (Polycarbonate, Poly(methyl methacrylate), etc.).

In the embodiment illustrated in FIG. 3, the window 32 and the ring 3 made in two separate parts. Nevertheless, in some embodiments, the window 32 and the ring 3 can be made in one part (monoblock). This allows limiting the risks of leakage at the junction between the ring 3 and the window 32.

When the window 32 and the ring 3 are two separate parts of the coupling interface, the window can be attached to the ring 3 by gluing, welding or any other technique allowing sealingly attaching the window 32 to the ring 3.

The window 32 may be covered with a layer of hydrophilic material. This makes it possible to limit the adhesion of air bubbles to the window 32.

The window 32 may be anti-reflective or have any other type of optical treatment in order to improve the transmission of the L.A.S.E.R. beam according to its wavelength.

2.3. Channels

The coupling interface also comprises two tubular through channels arranged in the side wall 31 of the ring 3.

Each through channel 35, 36 opens on the inner face of the side wall 31 of the ring, and extends radially outwardly perpendicular to the axis A-A'.

Each channel allows the connection of a remote device to the coupling interface via a respective nozzle:

A first channel 36 (called "irrigation channel") allows the connection of the coupling interface to an irrigation device for the infusion of liquid into the interior space 37, A second channel 35 (called "aspiration channel") allows the connection of the coupling interface to an aspiration device for the generation of a vacuum in the interior space 37.

Preferably, the irrigation channel 36 extends under the plane containing the window 32.

The aspiration channel 35 preferably opens on the inner face of the side wall 31 at the circular groove 33, that is to say, at the plane containing the window 32. This makes it possible to guarantee that the liquid comes into contact with the window 32 during the filling of the interior space 37.

In the embodiment illustrated in FIG. 3, the first and second channels 35, 36 are disposed one above the other so that the nozzles—connected to the channels on the one hand and to the irrigation and aspiration devices on the other hand—are located on one and the same side of the coupling interface, this side corresponding to the temporal side of the patient's head so that the nozzles do not come into contact with the nose bridge.

Advantageously, the irrigation channel 35 may have a diameter smaller than the diameter of the aspiration channel 36. The irrigation and aspiration devices being intended to be activated simultaneously, this difference in diameter makes it possible to keep a slight vacuum during the filling of the interior space 37 with liquid, and thus to ensure the sealing of the coupling interface during this step.

For example, in the embodiment illustrated in FIG. 3, the diameter of the irrigation channel 35 is chosen equal to 0.5 mm, and the diameter of the aspiration channel 36 is chosen equal to 1 mm.

3. Principle of Operation

Figure 5:
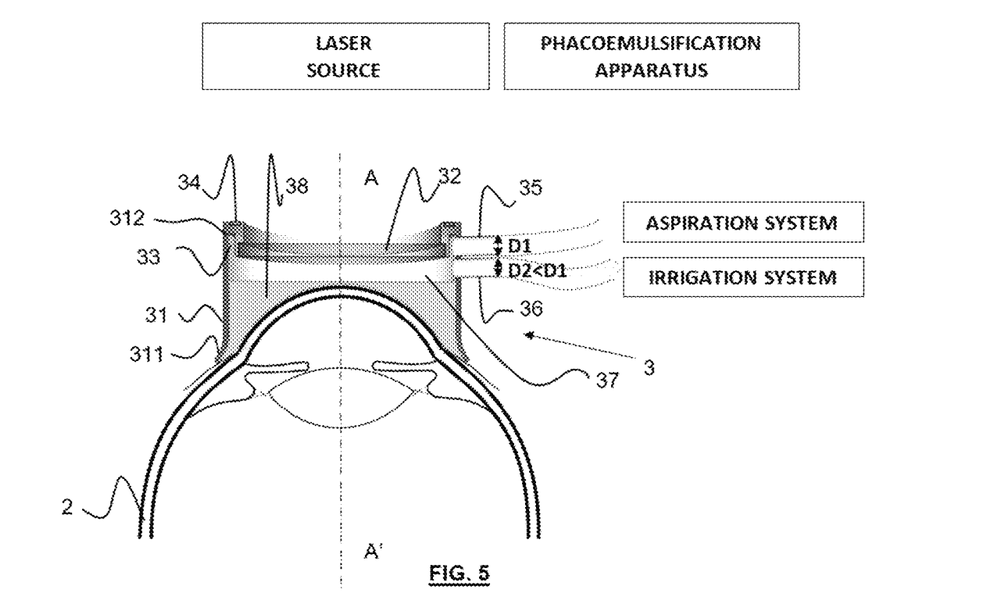
Figure 6:
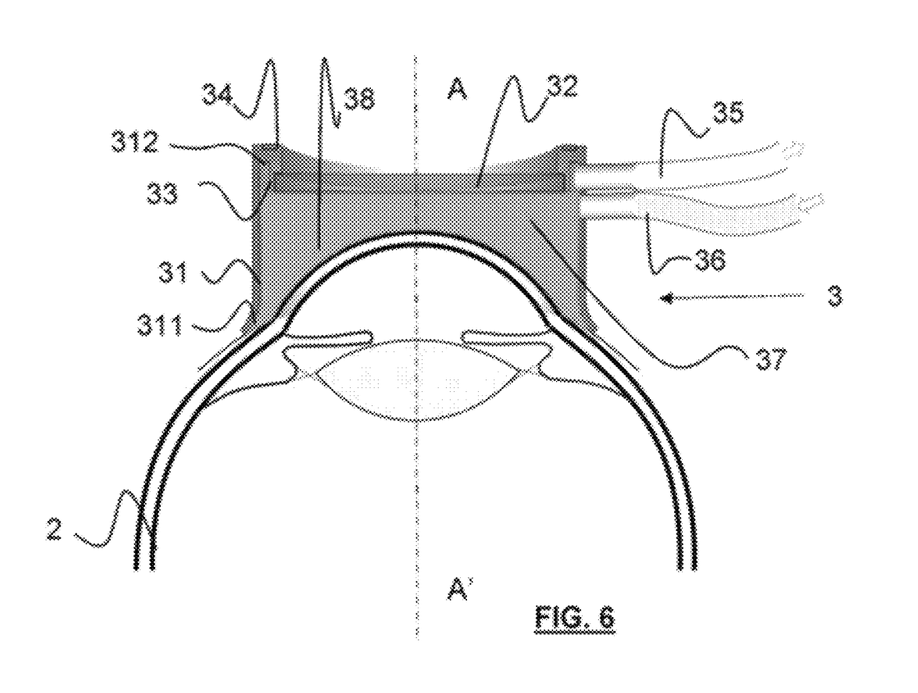
Figure 7:
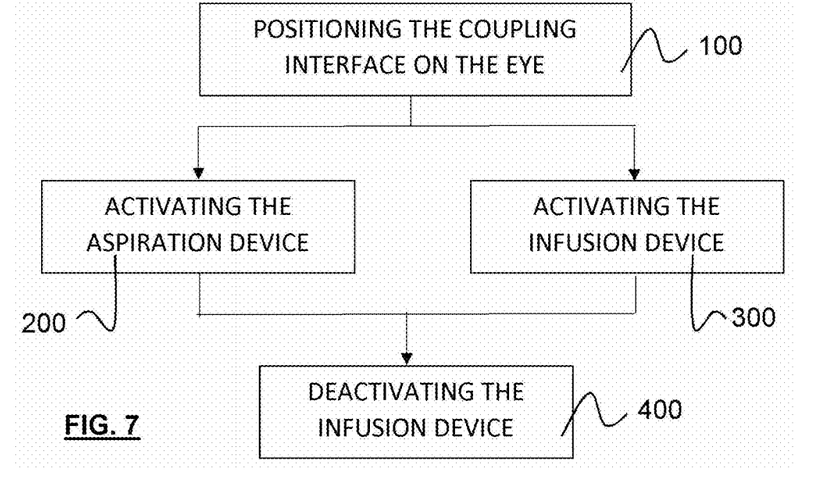
FIG. 7 illustrates a method for installing the coupling interface according to the invention.

The principle of operation of the coupling interface according to the invention will now be described in more detail with reference to the coupling device represented in FIGS. 3, 5 and 6, and to the method illustrated in FIG. 7. It is assumed that the first and second channels 35, 36 have been previously connected to the aspiration and irrigation device (not represented) via nozzles.

In a first step 100, the practitioner positions the ring 3 of the coupling interface on the eye 2, and centers it prior to the implementation of the laser treatment.

In a second step 200-300, the practitioner simultaneously activates the liquid aspiration device and the liquid irrigation device:
- the activation of the aspiration device allows creating a vacuum in the interior space 37 which exerts the suction, while
- the activation of the irrigation device allows filling the interior space 37 with liquid necessary to cover the corneal dome and reduce the corneal diopter.

As indicated above, the fact that the diameter of the irrigation channel 35 is cleverly chosen to be smaller in size (typically 0.5 mm) relative to the diameter of the aspiration channel 36 (typically 1 mm) allows holding a slight vacuum during the infusion of liquid, and thus ensuring the sealing of the coupling interface during this second step.

The enclosed interior space 37 defined between the cornea 2, the side wall 31 and the window 32 is filled in 1 to 2 seconds and simultaneously the air is aspired, creating a sufficient vacuum for the suction in 2 to 3 seconds.

The filling is thus complete very quickly and without any manipulation, and there is no air between the closing window 32 and the cornea 2, the residual air being confined in the circular bubble trap 33, into which the aspiration channel 35 terminates.

In addition, the aspiration circuit contains a volume of gas smaller than the traditional coupling interfaces, since part of this gas is replaced by non-compressible liquid simultaneously with the aspiration, which increases the speed of obtaining a firm holding by the suction.

Once the liquid is in contact with the window, the practitioner deactivates the irrigation device, while keeping the aspiration device activated (step 400).

The end of the laser source can then be attached to the coupling interface, without any contact between the end of the laser source and the liquid 38.

4. Conclusions

The surgical procedures performed in ophthalmology and using a laser source (in particular femtosecond laser) typically use a system for holding the eyeball, which must be active throughout the entire duration of exposure of the patient to the laser beam.

Indeed, the risk would be that, in case of unexpected and unexpected movement of the eyeball, the beam reaches areas not supposed to be affected and generates more or less serious lesions of the intraocular structures.

The holding of the eyeball with a device of known geometry, is also a method for precisely knowing the position in the space of the eyeball in order to precisely direct the laser beam on its target.

The holding of the eyeball is therefore a primordial step and the devices used, called coupling interfaces, are of paramount importance.

However, the holding of the eyeball implies a contact between a foreign body and the surface of the eyeball, as well as the application of a force opposing the movements. This position cannot be held for a long time and it is commonly accepted that the duration for which the patient's eye remains sucked to a coupling interface should not exceed two to three minutes. Beyond that, the discomfort for the patient and the risks caused by overpressure on the eyeball become unacceptable.

This limited time must be largely dedicated to the exposure to the laser beam, which performs some key steps of the surgical procedure. Therefore, the longer the time dedicated to placing the coupling interface, the shorter the time of exposure to the laser.

It is therefore essential to simplify this action as much as possible, in order to reduce the time, but also to increase comfort of the patient and to reduce the risks.

Finally, the possibility of using less consumable material, and therefore of making considerable savings, will allow this device to be accessible to the greatest number.

The new coupling interface described previously, allows providing all these advantages.

The reader will understand that many modifications can be made to the invention described above without physically departing from the new teachings and advantages described herein.

For example in the foregoing description, the coupling interface was decoupled from the end of the laser source, the patient treatment procedure comprising a step of placing the end of the laser source on the interface. Alternatively, the coupling interface may be secured to the end of the laser source, the step of centering the interface on the patient's eye being in this case performed automatically by using means known to those skilled in the art.

Consequently, all modifications of this type are intended to be incorporated within the scope of the appended claims.

The invention claimed is:

1. A coupling interface between a laser source and a tissue to be treated, wherein the coupling interface comprises:
    a ring including:
        a side wall,
        a proximal end intended to come into contact with the tissue to be treated, and
        a distal end intended to receive the end of the laser source,
    a window transparent to a laser beam generated by the laser source, said window being sealingly mounted on the ring so as to close the distal end of the ring,
    an aspiration through channel extending between an inner face and an outer face of the side wall, wherein the aspiration through channel is connected to an aspiration module for allowing the generation of a vacuum in an interior space defined between the window and the side wall, and
    an irrigation through channel extending between the inner and outer faces of the side wall, wherein the irrigation through channel is connected to an irrigation module for allowing the infusion of liquid into the interior space, and wherein an internal diameter of the irrigation through channel is smaller than an internal diameter of the aspiration through channel.

2. The coupling interface according to claim 1, which further comprises a bubble trap extending around the window.

3. The coupling interface according to claim 2, wherein the bubble trap consists of a circular inner groove extending between the side wall and the window.

4. The coupling interface according to claim 1, wherein the aspiration through channel extends in a plane containing the window.

5. The coupling interface according to claim 1, wherein the window is covered with a layer of hydrophilic material.

6. The coupling interface according to claim 2, wherein the window has a non-planar geometry with parallel faces, having for example a concavity allowing better evacuation of the bubbles toward the bubble trap.

7. The coupling interface according to claim 1, wherein the window has a non-planar geometry with non-parallel faces, having for example a biconvexity, thus giving the window an optical role.

8. The coupling interface according to claim 1, wherein the ring includes a flared neck of a frustoconical shape curved outwardly at its proximal end, the flared neck being capable of being applied to the outer surface of the tissue to be treated.

9. The coupling interface according to claim 1, wherein the window is attached to the ring by gluing.

10. A device comprising a laser source and a phacoemulsification apparatus, the device including an irrigation system and an aspiration system, wherein the device further comprises a coupling interface between the laser source and a tissue to be treated, said coupling interface having:
   a ring including:
      a side wall,
      a proximal end intended to come into contact with the tissue to be treated, and
      a distal end intended to receive the end of the laser source,
   a window transparent to a laser beam generated by the laser source, said window being sealingly mounted on the ring so as to close the distal end of the ring,
   an aspiration through channel extending between an inner face and an outer face of the side wall, wherein the aspiration through channel is connected to an aspiration module for allowing the generation of a vacuum in an interior space defined between the window and the side wall, and
   an irrigation through channel extending between the inner and outer faces of the side wall, wherein the irrigation through channel is connected to an irrigation module for allowing the infusion of liquid into the interior space.

11. The device according to claim 10, wherein the aspiration through channel of the coupling interface is connected to the aspiration system, and the irrigation through channel is connected to the irrigation system.

12. The device according to claim 10, wherein the device comprises a single aspiration and irrigation system including a pump and a vacuum sensor, said single aspiration and irrigation system being used for both a laser treatment and a phacoemulsification treatment.

13. The device according to claim 10, wherein the coupling interface further comprises a bubble trap extending around the window.

14. The device according to claim 13, wherein the bubble trap consists of a circular inner groove extending between the side wall and the window.

15. The device according to claim 10, wherein the aspiration through channel extends in a plane containing the window.

16. The device according to claim 13, wherein the window has a non-planar geometry with parallel faces, having for example a concavity allowing better evacuation of the bubbles toward the bubble trap.

17. The device according to claim 10, wherein the window has a non-planar geometry with non-parallel faces, having for example a biconvexity, thus giving the window an optical role.

18. The device according to claim 10, wherein the ring includes a flared neck of a frustoconical shape curved outwardly at its proximal end, the flared neck being capable of being applied to the outer surface of the tissue to be treated.

19. The device according to claim 10, wherein the internal diameter of the irrigation through channel is smaller than the internal diameter of the aspiration through channel.

* * * * *